United States Patent [19]

Ghosez et al.

[11] 4,041,077
[45] Aug. 9, 1977

[54] N-BENZYL-2,2-DIMETHOXY-ACETAMIDES

[75] Inventors: Léon Ghosez; Guy Rossey, both of Heverlee; Freddy Didderen, Petit-Rechain, all of Belgium

[73] Assignee: U C B, Societe Anonyme, Saint-Gilles-lez-Brussels, Belgium

[21] Appl. No.: 689,148

[22] Filed: May 24, 1976

[30] Foreign Application Priority Data

May 27, 1975 United Kingdom .............. 23184/75
May 27, 1975 United Kingdom .............. 23183/75

[51] Int. Cl.² .............. C07C 103/127; C07C 103/34
[52] U.S. Cl. .............. 260/562 R; 260/288 R; 260/289 R; 260/561 B; 260/562 P; 260/562 A
[58] Field of Search .......... 260/562 R, 562 P, 562 A, 260/561 B

[56] References Cited

PUBLICATIONS

Blazevic et al., J. Chem. Soc. (c), 1968, pp. 1704–1708.

Kazmierczak et al., Chem. Abstracts, 69 (1968), No. 43590j.

*Primary Examiner*—Arthur P. Demers
*Attorney, Agent, or Firm*—Wenderoth, Lind & Ponack

[57] ABSTRACT

N-benzyl-2,2-dimethoxy-acetamides having the formula

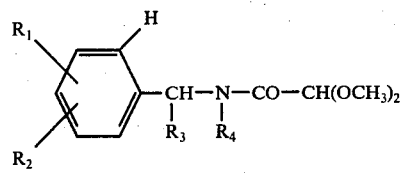

and processes for preparing the same. These acetamides are useful for the production of 2H-3-isoquinolones by acid cyclization and said 2H-3-isoquinolones are in turn useful as starting materials inter alia in the synthesis of 1,4-dihydro-1,4-etheno-isoquinolin-3(2H)ones, which are valuable chemotherapeutic agents as disclosed in U.S. Pat. No. 3,781,436.

21 Claims, No Drawings

N-BENZYL-2,2-DIMETHOXY-ACETAMIDES

The present invention relates to new N-benzyl-2,2-dimethoxyacetamides and to the preparation thereof.

The new N-benzyl-2,2-dimethoxy-acetamides according to the present invention are compounds of the general formula:

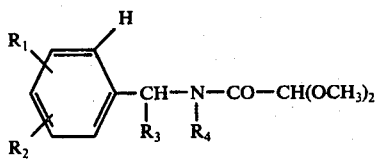

(I)

wherein
- $R_1$ and $R_2$ each represents a hydrogen atom, a halogen atom, an alkyl radical having 1 to 6 carbon atoms, an alkoxy radical having 1 to 6 carbon atoms or an aryl radical, said aryl radical being optionally substituted by at least one halogen atom, alkyl radical having 1 to 6 carbon atoms or alkoxy radical having 1 to 6 carbon atoms,
- $R_3$ is a hydrogen atom, an alkyl radical having 1 to 6 carbon atoms, an aryl, an aralkyl or a cycloalkyl radical, said aryl, aralkyl or cycloalkyl radicals being optionally ring-substituted by at least one halogen atom, alkyl radical having 1 to 6 carbon atoms or alkoxy radical having 1 to 6 carbon atoms, and
- $R_4$ is a hydrogen atom, an alkyl radical having 1 to 6 carbon atoms, an aryl or an aralkyl radical, said aryl or aralkyl radicals being optionally ring-substituted by at least one halogen atom, alkyl radical having 1 to 6 carbon atoms or alkoxy radical having 1 to 6 carbon atoms.

As examples of halogen atoms, there may be mentioned chlorine, bromine, fluorine and iodine atoms, preferably chlorine and bromine atoms and more preferably chlorine atoms.

As examples of alkyl radicals, there may be mentioned the methyl, ethyl, propyl, butyl, pentyl and hexyl radicals, which may be straight-chained or branched.

As examples of alkoxy radicals, there may be mentioned the methoxy, ethoxy, propoxy, butoxy, pentoxy and hexoxy radicals, which may be straight-chained or branched.

As examples of aryl radicals, there may be mentioned phenyl and naphthyl radicals, which may be substituted by at least one of the substituents selected from halogen atoms, alkyl radicals and alkoxy radicals, such as those defined above.

As examples of aralkyl radicals, there may be mentioned benzyl and phenethyl radicals, which may be ring-substituted by at least one of the substituents selected from halogen atoms, alkyl radicals and alkoxy radicals, such as those defined above.

As examples of cycloalkyl radicals, there may be mentioned cyclopentyl and cyclohexyl radicals, which may be substituted by at least one of the substituents selected from halogen atoms, alkyl radicals and alkoxy radicals, such as those defined above.

The preferred compounds of the invention are those of the above-mentioned general formula I in which:
- $R_1$ represents a hydrogen, halogen, $C_1$-$C_4$-alkyl or $C_1$-$C_4$-alkoxy, $R_2$ is hydrogen or $C_1$-$C_4$-alkyl,
- $R_3$ is hydrogen, $C_1$-$C_4$-alkyl, aryl or aralkyl, and
- $R_4$ is hydrogen, $C_1$-$C_4$-alkyl, aryl or aralkyl.

The new N-benzyl-2,2-dimethoxy-acetamides of general formula (I) according to the present invention can be prepared by reacting a benzylamine of formula (II) with 2,2-dimethoxyacetyl chloride of formula (III) at low temperature in solution in an inert organic solvent in the presence of an acid acceptor such as an organic tertiary amine, according to the following equation:

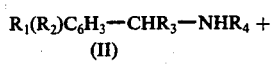

(II)

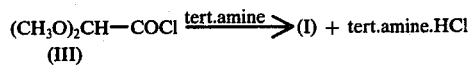

(III)

In this equation, $R_1$, $R_2$, $R_3$ and $R_4$ have the same meanings as above.

2,2-Dimethoxyacetyl chloride (III) is an unstable compound. For this reason, according to a preferred method of carrying out the process according to the present invention, 2,2-dimethoxyacetyl chloride is prepared in situ, starting from 2,2-dimethoxyacetic acid of formula (IV) and 3-chloro-N,N,2-trimethyl-allylamine of formula (V) at a low temperature in an inert organic solvent such as methylene chloride according to the following equation:

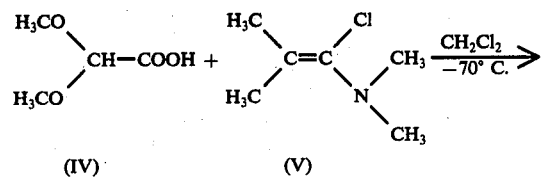

(IV)         (V)

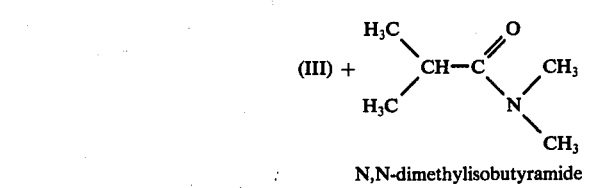

N,N-dimethylisobutyramide

Then, without isolating the N,N-dimethylisobutyramide formed as a by-product, the 2,2-dimethoxyacetyl chloride (III) thus obtained is reacted, in the same reaction vessel, with a benzylamine of formula (II) according to the above-described reaction scheme.

The preparation of 2,2-dimethoxyacetyl chloride is carried out at a temperature in the region of −70° C., whereas the formation of the amide (I) is carried out first at a temperature in the region of −50° to −60° C., whereafter the temperature is allowed to rise to ambient temperature, while stirring, in order to complete the reaction.

The preferred solvent is methylene chloride. However, in general, other chlorinated aliphatic or aromatic hydrocarbons may also be used.

Secondary N-benzyl-2,2-dimethoxy-acetamides of formula (I), wherein $R_4$ is hydrogen, can also be prepared by reacting a benzylamine of the formula (VI) with methyl 2,2-dimethoxyacetate (VII), optionally in the presence of sodium methylate, according to the following equation:

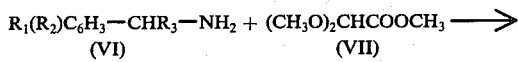

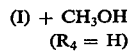

wherein $R_1$, $R_2$ and $R_3$ have the same meanings as above.

Methyl 2,2-dimethoxyacetate (VII) can be prepared by the following method (cf. H. Gross, J. Freiberg, Chem.Ber.,99,(1966),3260–67):

In a three-necked 2 liter round-bottomed flask, equipped with a condenser with a calcium chloride tube, a constant pressure dropping funnel and a mechanical stirrer, 32.2 g. sodium are reacted on 300 ml. of absolute methanol. The mixture is heated to reflux temperature and 51.6 g. (0.4 mole) 2,2-dichloroacetic acid are added dropwise. The reaction mixture is boiled under reflux for 5 hours. The solution is then cooled in an ice-bath and is neutralized with methanol saturated with hydrogen chloride, using phenolphthalein as indicator, the temperature being maintained at 30° C. The temperature is again reduced to below 20° C. and 47.6 g. (0.4 mole) freshly distilled thionyl chloride are added thereto. The reaction mixture is left to stand overnight, whereafter the sodium chloride formed is filtered off and the methanol is evaporated. The residue is then distilled in vacuo. The yield of methyl 2,2-dimethoxyacetate is 72% of theory; B.P. 64.5° C./15 mm.Hg.

IR: (film, cm$^-$) 3000, 2950 (CH$_3$), 2840 (OCH$_3$), 1760 (CO), 1440

NMR: (CCl$_4$ + tetramethylsilane): 3.37 (singlet 6H); 3.72 (singlet 3H); 4.70 (singlet 1H)

In order to prepare the secondary N-benzyl-2,2-dimethoxyacetamides ($R_4$ = H) according to the present invention, there are stirred together, at ambient temperature, equimolar quantities of the ester and of the amine or the amine is introduced into the ester, if necessary, in the presence of a small excess of sodium methylate in order to displace the equilibrium of the reaction. The course of the reaction can be followed by infrared spectroscopy. In the case of certain compounds, the reaction mixture solidifies and a recrystallization is carried out, for example from petroleum ether. The amide is thus obtained in the form of fine needles. The solution in petroleum ether can also be concentrated and the residue distilled in vacuo; the amide is thus obtained in the form of a viscous oil which, in some cases, crystallizes.

Examples of benzylamines of the formula:

(II) or (VI)

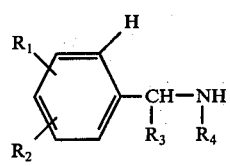

include the following compounds:
benzylamine
α-methylbenzylamine
α-n-butylbenzylamine
2-chlorobenzylamine
3-methoxybenzylamine
3,4-dimethoxybenzylamine
4-methylbenzylamine
benzhydrylamine
α-phenylmethyl-benzylamine
N-benzyl-N-methylamine
N,N-dibenzylamine
N-benzyl-N-n-butylamine
N-benzyl-N-phenylamine
N-(3,4-dimethoxybenzyl)-N-(3,4-dimethoxyphenethyl)-amine.

The N-benzyl-2,2-dimethoxyacetamides of formula (I) according to the present invention are cyclized, by heating in concentrated mineral acids, into 2H-3-isoquinolones. The latter are valuable intermediates for the preparation of pharmaceutical products, dyestuffs, antioxidants and photographic materials.

Thus, for example, these 2H-3-isoquinolones can be used as starting materials in the production of 1,4-dihydro-1,4-ethenoisoquinolin-3(2H)-ones according to the process described in British Patent Specification No. 1,333,564. The usefulness of these 1,4-dihydro-1,4-etheno-isoquinolin-3(2H)-ones as chemotherapeutic agents valuable in the treatment of disorders of the central nervous system in man, i.e. troubles of wakefulness, disorders or equilibrium and vertigo, psychosomatic syndromes, neuroses, disorders due particularly to senility, delirous and hallucinatory psychoses and as an antalgic, is disclosed in U.S. Pat. No. 3,781,436.

The following Examples are given for the purpose of illustrating the present invention:

EXAMPLE 1.

N-benzyl-2,2-dimethoxy-acetamide.

10.7 g. (0.1 mole) benzylamine and 13.4 g. (0.1 mole) methyl 2,2-dimethoxyacetate are introduced into an Erlenmeyer flask and left to react for 24 hours. The reaction mixture solidifies. The crude product is crystallized from petroleum ether to give 12.8 g. N-benzyl-dimethoxyacetamide in the form of fine white needles. A sample intended for analysis is sublimed at 65° C./0.03 mm.Hg. The yield is 61% of theory; M.P. 51° C.

Infrared spectrum (KBr) (cm$^-$): 3300 (NH), 2940, 2830 (OCH$_3$), 1670 + 1520 (CONH), 1460, 1115, 1070 (CO); (CCl$_4$) (cm$^-$): 3445 (NH), 2850 (OCH$_3$), 1695 + 1520 (CONH), 1120, 1075 (CO), 695.

NMR (CDCl$_3$): 7.27 (6H, singlet, H$_a$) 4.70 (1H, singlet, H$_b$) 4.4 (2H, doublet, H$_c$, J:6Hz) 3.37 (6H, singlet, H$_d$)

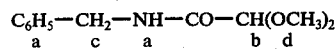

Mass spectrum: m/e 209 (M+), 178 (-Ch$_3$OH), 146, 121, 118, 106 (amine), 91 (C$_7$H$_7$+), k75.47 (M* 29.5)

Analysis: C$_{11}$H$_{15}$NO$_3$ (M.W. 209.248): calculated: C 69.14%; H 7.12%; N 6.69%; found: 69.3%; 7.3%; 6.63%

EXAMPLE 2.

2,2-Dimethoxy-N-(α-methylbenzyl)-acetamide.

10 g. (82.5 mmole) α-methylbenzylamine are contacted with 12 g. (90 mmole) methyl 2,2-dimethoxyacetate for 4 days. 60 ml. petroleum ether are then added thereto, the precipitated salt (benzyl-ammonium acetate; M.P. 145° C., 2.5 g.; 0.01 mole) is filtered off and the solvent is then eliminated. The 10 g. of viscous colorless residue obtained is distilled, for analysis, at 130°–135° C./0.1 mm.Hg. There are obtained 7.6 g. of colorless oil as product. The IR spectrum of the product before and after distillation is identical. The yield is 52% of theory of 2,2-dimethoxy-N-(α-methylbenzyl)-acetamide; B.P. 130°–135° C./0.1 mm.Hg.

Infrared spectrum (CCl$_4$) cm$^-$): 3440 (NH), 2850 (OCH$_3$), 1690 + 1520 (CONH), 1450, 1115, 1070, 700
NMR (CDCl$_3$): 7.3 (5H, singlet, H$_1$); 6.83 (1H, multiplet, H$_b$); 5.17 (1H, quintuplet, H$_c$, J:8Hz); 3.4 + 3.33 (6H, two singlets, H$_d$); 1.5 (3H, doublet, H$_e$, J:8Hz); 4.7 (1H, singlet, H$_f$)

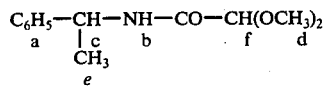

Mass spectrum: m/e 223 (M+), 191 (—CH$_3$OH), 160, 132, 120, 121, 105 (tropylium), 75, 47 (M* 29.5)

Analysis: C$_{12}$H$_{17}$NO$_3$ (M.W. 223.274): calculated: C 64.55%; H 7.67%; N 6.27% found: 64.60%; 7.71%; 6.24%

EXAMPLE 3.

N-(α-n-butylbenzyl)-2,2-dimethoxy-acetamide.

The method of Example 2 is followed, but α-methylbenzylamine is replaced by α-n-butyl-benzylamine.

In this manner, there is obtained N-(α-n-butylbenzyl)-2,2-dimethoxy-acetamide in a yield of 68% of theory; B.P. 134–136° C./0.001 mm.Hg.

EXAMPLE 4.

N-(2-chlorobenzyl)-2,2-dimethoxyacetamide.

7.1 g. (0.05 mole) 2-chlorobenzylamine are contacted with 6.7 g. (0.05 mole) methyl 2,2-dimethoxyacetate for a period of 24 hours. 60 ml. petroleum ether are added thereto, the precipitated salt is filtered off and the solvent is eliminated. The residue is distilled, for analysis, at 140°–145° C./0.05 mm.Hg. There are obtained 8.5 g. N-(2-chlorobenzyl)-dimethoxyacetamide in the form of a colorless oil which solidifies at about 30°C. The yield is 71% of theory; B.P. 140°–145° C./0.05 mm.Hg.

Infrared spectrum (CCl$_4$) (cm$^-$): 3450 (NH), 2950, 2850 (OCH$_3$), 1690 + 1510 (CONH), 1440, 1190, 1125 + 1070 (CO), 985

NMR (CCl$_4$): 7.67-7.0 (5H, multiplet, H$_a$); 4.60 (1H, singlet, H$_b$); 4.45 (2H, doublet, H$_c$, J:6Hz); 3,27 (6H, singlet, H$_d$);

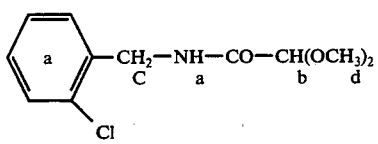

Mass spectrum: m/e 243 (M+), 208 (—Cl), 155, (amine), 125 (tropylium), 75, 47 (M* 29.5).

Analysis: calculated: C 54.21%; H 5.79%; N 7.74%; found: 54.09%; 5.65%; 5.71%

EXAMPLE 5.

2.2-Dimethoxy-N-(3methoxybenzyl-actamide.

8 g. (58 mmole) 3-methoxybenzylamine and 9 g. (66 mmole) methyl 2,2-dimethoxyacetate are contacted for 48 hours. 70 ml. petroleum ether are then added, the insoluble material is filtered off and the solvent is eliminated. The residual oil is distilled at 145°–147° C./0.001 mm.Hg. There are obtained 10 g. of 2,2-dimethoxy-N-(3-methoxybenzyl)- acetamide in the form of a colorless viscous oil. The yield is 72% of theory; B.P. 145°–147° C./0.001 mm.Hg.

NMR (CDCl$_3$): 7.4-6.65 (5H, multiplet, H$_a$); 4.7 (1H, singlet, H$_b$); 4.4 (2H, doublet, H$_c$); 3.77 (3H, singlet, H$_d$, J=6Hz); 3.37 (6H, singlet, H$_e$)

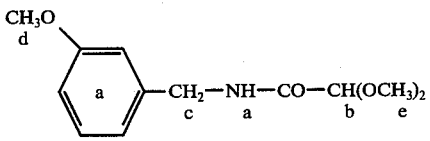

Mass spectrum: m/e 239 (M+), 207 (—CH$_3$OH), 176 (CO), 151, 148, 136 (amine), 121 (tropylium), 91, 75, 47, M* 29.5.

Analysis: C$_{12}$H$_{17}$NO$_4$ (M.W. 239.274): calculated: C 60.23%; H 7.16%; N 5.85%; found: 60.20%; 7.20%; 5.81%

EXAMPLE 6.

2,2-Dimethoxy-N-(3,4-dimethoxybenzyl)-acetamide.

16.7 g. (0.1 mole) 3,4-dimethoxybenzylamine are contacted with 13.4 g. (0.1 mole) methyl 2,2-dimethoxyacetate for 3 hours. The reaction mass solidifies. The crude product is recrystallized from about 1 liter of a light petroleum ether fraction to give 19.4 g. of 2,2-dimethoxy-N-(3,4-dimethoxybenzyl)-acetamide in the form of white needles. A sample intended for analysis is sublimed at 70° C./0.03 mm.Hg. The yield is 72% of theory. The product has a melting point of 60° C.

Infrared spectroscopy (CCl$_4$) (cm$^-$): 3440 (NH), 2950 (CH$_3$), 2850 (OCH$_3$), 1680 + 1510 (CONH), 1600, 1460, 1115 +1070 (CO)

NMR (CDCl$_3$): 6.84 (4H, singlet, H$_a$); 4.72 (1H, singlet, H$_b$); 4.38 (2H, doublet, H$_c$, J=6Hz); 3.87 (6H, singlet, H$_d$); 3.39 (6H, singlet, H$_3$)

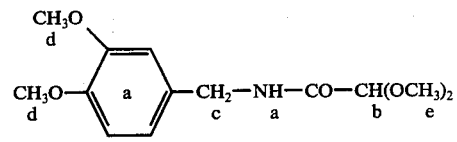

Mass spectrum: m/e 269 (M+), 237 (—CH$_3$OH), 222, 206 (M* at 209), 181, 166 (amine), 151 (tropylium), 75, 47, 31 (M* at 29.5)

Analysis: C$_{13}$H$_{19}$NO$_5$ (M.W. 269.3): calculated: C 57.98%; H 7.11%; N 5.20%; found: 57.95%; 7.15%; 5.17%

EXAMPLE 7.

2,2-Dimethoxy-N-(4-methylbenzyl)-acetamide.

10 g. (82.5 mmole) 4-methylbenzylamine are contacted with 12 g. (90 mmole) methyl 2,2-dimethoxy acetate for a period of 48 hours. 100 ml. petroleum ether are added, the insoluble material is filtered off and the solvent is eliminated. There are obtained 17 g. of crude product which is distilled at 158° C./0.001 mm.Hg. The product is in the form of a viscous, colorless oil which crystallizes upon standing. The yield is 13 g. (72% of theory) 2,2-dimethoxy-N-(4-methylbenzyl)acetamide. A sample for analysis is obtained by recrystallization from petroleum ether. The yield of crude product is 92% of theory and the yield of distilled product is 72% of theory; M.P. 45.8° C.; B.P. 158°–160° C./0.001 mm.Hg.

Infrared spectroscopy (CCl$_4$) (cm): 3440 (NH), 2850 (OCH$_3$), 1690 + 1515 (CONH), 1115 + 1070 (CO)

NMR (CDCl$_3$): 7.17 (5H, singlet, H$_a$); 4.7 (1H, singlet, H$_b$); 4.41 (2H, doublet, H$_c$, J:6Hz); 3.39 (6H, singlet, H$_d$); 2.33 (3H, singlet, H$_e$)

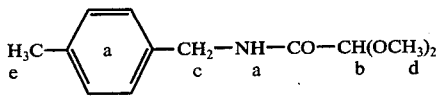

Mass spectrum: m/e 223 (M+), 191 (—CH$_3$OH) (M* 164), 160, 135, 132 (CO), 120 (amine), 105 (tropylium), 75, 47, M* 29.5.

Analysis: C$_{12}$H$_{17}$NO$_3$ (M.W. 223.274): calculated: C 64.55%; H 7.67%; N 6.27%; found: 64.53%; 7.73%; 6.17%

EXAMPLE 8.

N-benzhydryl-2,2-dimethoxy-acetamide.

Into a 50 ml. round-bottomed flask equipped with a magnetic stirrer and surmounted by a bent tube leading to a sulfuric acid trap, there are introduced 3.5 g. (0.019 mole) benzhydrylamine, 2.68 g (0.02 mole) methyl 2,2-dimethoxy-acetate and 1.5 g. (0.03 mole) sodium methylate. The reaction mixture is stirred for 90 minutes. The reaction is slightly exothermal and the reaction mixture becomes colored. 40 ml. of a mixture of isopropanol and water are added and the mixture is left to crystallize in the cold. Crystals are thus formed which are filtered off and recrystallized from petroleum ether. There are obtained 3.3 g. (61% of theory) N-benzhydryl-2,2-dimethoxyacetamide in the form of fine white needles. A sample for analysis is obtained by sublimation at 70° C./0.03 mm.Hg. and recrystallization from petroleum ether.

Yield without the use of sodium methylate: nil
Yield with the use of sodium methylate: 61% of theory
The product melts at 74.6°–77° C.

Infrared spectroscopy (KBr) (cm$^-$): 3340 (NH), 2870 (OCH$_3$), 1655 + 1525 (CONH), 115 + 1060 (CO), 690

NMR (CDCl$_3$): 7.2 (11H, singlet, 2 C$_6$H$_5$ + NH, H$_a$); 6.23 (1H, doublet, J = 8Hz, H$_b$); 4.7 (1H, singlet, H$_c$); 3.36 (6H, singlet, H$_d$)

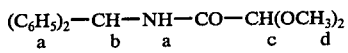

Mass spectrum: m/e 285 (M+), 253 (—CH$_3$OH) (M+ 225), 222 (-OCH$_3$), 182 (amine) 167 (tropylium), 121, 104, 75, 47, M* 29.5

Analysis: C$_{17}$H$_{19}$NO$_3$ (M.W. 285.346): calculated: C 71.55%; H 6.71%; N 4.90%; found: 71.50%; 6.74%; 4.86%

EXAMPLE 9.

2,2-Dimethoxy-N-(α-phenylmethyl-benzyl)-acetamide.

The method of Example 8 is followed, but α-phenyl-benzylamine is replaced by α-phenylmethyl-benzylamine and use is made of a catalytic amount of sodium methylate. All other conditions remain unchanged. 2,2-Dimethoxy-N-(α-phenylmethyl-benzyl)-acetamide is obtained with a yield of 45% of theory. It melts at 108°–110° C. after recrystallization from isopropanol.

Analysis: C$_{18}$H$_{21}$NO$_3$: calculated: C 72.5%; H 7.05%; N 6.7%; found: 70.62%; 7.07%; 6.4%

Infrared spectroscopy (KBr) (cm$^-$): 3320 (NH), 1672 (CO amide), 1528 (NH), 758, 700 (benzyl).

NMR (CDCl$_3$): 6.7-7.2 (11H, multiplet, 2 C$_6$H$_5$ + NH, H$_a$); 5-5.6 (1H, multiplet, Ar-C$H$-N, H$_b$); 4.65 (1H, singlet, —C$H$(methoxy)$_2$, H$_c$); 3.2 (6H, singlet, OCH$_3$, H$_d$); 3.08 (2H, singlet, CH$_2$Ph, H$_e$)

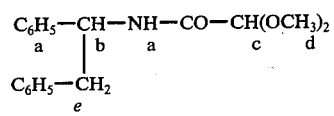

EXAMPLE 10.

N-benzyl-2,2-dimethoxy-acetamide.

The reaction apparatus used comprises a first round-bottomed flask equipped with a magnetic stirrer, a constant pressure dropping funnel, a nitrogen supply tube and a tube connected to a second jacketed constant pressure funnel mounted on a second round-bottomed flask equipped with a magnetic stirrer and a nitrogen exit tube. The two round-bottomed flasks, as well as the second jacketed constant pressure funnel, are cooled to a low temperature using a bath of isopropanol and dry ice.

A nitrogen current is passed through the apparatus dried with the flame. Into the first flask are introduced 10 ml. methylene chloride (dried over phosphorus pentoxide), 0.1 ml. triethylamine and 1.966 g. (0.0147 mol) 3-chloro-N,N,2-trimethyl-allylamine. The mixture is cooled to −70° C. and, by means of the first constant pressure dropping funnel, there is added dropwise, over the course of an hour, a solution of 1.769 g. (0.0147 mole) 2,2-dimethoxyacetic acid in 10 ml. methylene chloride. Thereafter, the reaction mixture is further stirred for 90 minutes.

Into the second flask are introduced 15 ml. methylene chloride, 1.575 g. (0.0147 mole) freshly distilled benzylamine and an excess of triethylamine (2 ml., dried over potassium hydroxide). The contents of the first flask (solution of the acid chloride and isobutyramide formed in methylene chloride) are then passed into the second jacketed constant pressure funnel cooled to −70° C., whereafter this solution is slowly added to the amine solution in the second flask maintained at a temperature of −50° C. The reaction mixture is then allowed to warm up to ambient temperature, while stirring, over the course of 2 hours.

The solvent is then evaporated, 170 ml. of dry diethyl ether are added to the evaporation residue and the mixture is heated under reflux for 10 minutes. The precipitate is filtered off and the solvent is evaporated off from the filtrate. A slightly yellow liquid is obtained from which the major part of the isobutyramide and the excess of triethylamine are removed by distillation in vacuo (0.2 mm.Hg.). The amide is taken up in the minimum amount of anhydrous diethyl ether and left to stand overnight in a refrigerator. The N-benzyl-2,2-dimethoxyacetamide formed crystallizes out in the form of white needles. The yield is 2.06 g. (67% of theory) (crystallized product 61% of theory). The product melts at 51°–52° C.

The compound prepared is identical with that prepared in Example 1.

EXAMPLE 11.

N-benzyl-2,2-dimethoxy-N-methyl-acetamide.

The reaction apparatus used is the same as that employed in Example 10.

Into the first flask are placed 10 ml. methylene chloride (dried over phosphorus pentoxide) and 4.580 g. (0.0343 mol) 3-chloro-N,N2-trimethyl-allylamine. By means of the first constant pressure funnel, there is introduced dropwise, while stirring, 4.117 g. (0.0343 mole) 2,2-dimethoxyacetic acid dissolved in 10 ml. methylene chloride over the course of one hour. Subsequently, stirring is continued for 90 minutes.

Into the second flask, there are introduced 15 ml. methylene chloride, 4.157 g. (0.0343 mole) N-benzyl-N-methylamine (freshly distilled) and an excess of triethylamine (5 ml. dried over potassium hydroxide). Thereafter, the contents of the first flask (solution of the acid chloride and of isobutyramide formed in methylene chloride) are passed into the second jacketed constant pressure funnel, cooled to −70° C. and this solution is slowly added dropwise into the second flask over the course of 45 minutes, while maintaining the temperature at −60° C. The reaction mixture is allowed to warm up to ambient temperature, while stirring, over the course of 6 hours.

The solvent is then evaporated, 200 ml. of anhydrous diethyl ether are added to the residue and the reaction mixture is heated at reflux temperature for 10 minutes. The triethylamine hydrochloride formed is then filtered off. The solvent present in the filtrate is then evaporated off to give a syrupy product with a red-brown color. The greater part of the isobutyramide and of the triethylamine are eliminated under reduced pressure (0.2 mm.Hg.) and the residue is distilled in vacuo. There is thus obtained N-benzyl-2,2-dimethoxy-N-methyl-acetamide, which has a boiling point of 103–105° C./0.01 mm.Hg. The yield is 5.943 g. (77.6% of theory).

Infrared spectrum (film) (cm−): 2930 (CH$_3$), 2830 (OCH$_3$), 1660 (C=O), 1490, 1450.

NMR spectrum CCl$_4$: 7.33 (singlet 5 H$_a$); 4.83 (singlet 1 H$_b$) 4.70 and 4.56 (2 singlets 2 H$_c$); 3.50 (singlet 6 H$_d$); 2.97 and 2.73 (2 singlets 3 H$_3$)

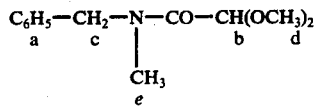

EXAMPLE 12.

N,N-dibenzyl-2,2-dimethoxy-acetamide.

Under the same working conditions as used in Example 10 but substituting N,N-dibenzylamine for N-benzylamine, there is obtained N,N-dibenzyl-2,2-dimethoxy-acetamide in a yield of 70% of theory; the compound melts at 73.5° C.

Infrared spectrum (CCl$_4$) (cm−): 2835 (CH$_3$), 1675, 1655, 1651 (C=O)

NMR spectrum (CCl$_4$ + tetramethylsilane): 7.27 (multiplet 10 H$_a$); 4.83 (singlet 1 H$_b$); 4.58, 4.40 (singlet 2 H$_c$, singlet 2 H$_c$); 3.48 (singlet 6 H$_d$)

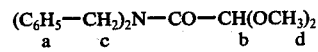

Mass spectrum: m/e 299 (M+), 91 (C$_7$H$_7$+), 75 (HC+OMe$_2$)

EXAMPLE 13.

Under the same working conditions as used in Example 10, but replacing N-benzylamine by an appropriately substituted benzylamine, the following N-benzyl-2,2-dimethoxy-acetamides according to the invention were prepared. Compounds I) to VII) are identical with those prepared in Examples 2 to 8. For each compound prepared, a physical constant, the method of purification and the benzylamine used as starting substance is given.

I. 2,2-dimethoxy-(N-alpha-methylbenzyl)-acetamide, B.P. 130°–135° C./0.1 mm.Hg., purified by distillation and prepared from alphamethylbenzylamine.

II. N-(alpha-n-butylbenzyl)-2,2-dimethoxy-acetamide, B.P. 134°–136° C./0.001 mm.Hg., purified by distillation and prepared from alpha-n-butylbenzylamine.

III. N-(2-chlorobenzyl)-2,2-dimethoxy-acetamide, B.P. 140°–145° C./0.05 /mm.Hg., purified by distillation and prepared from 2-chlorobenzylamine.

IV. 2,2-dimethoxy-N-(3-methoxybenzyl)-acetamide, B.P. 145°–147° C./0.001 mm.Hg., purified by distillation and prepared from 3-methoxybenzylamine.

V. 2,2-dimethoxy-N-(3,4-dimethoxybenzyl)-acetamide, M.P. 60° C., purified by crystallization from petroleum ether and prepared from 3,4-dimethoxybenzylamine.

VI. 2,2-dimethoxy-N-(4-methylbenzyl)-acetamide, M.P. 45.8; B.P. 158°C./0.001 mm.Hg., purified by distillation and crystallization from petroleum ether and prepared from 4-methylbenzylamine.

VII. N-benzhydryl-2,2-dimethoxy-acetamide, M.P. 74.6°–77° C., purified by crystallization from petroleum ether and by sublimation (70° C./0.03 mm.Hg.) and prepared from benzhydrylamine.

VIII. N-benzyl-N-n-butyl-2,2-dimethoxy-acetamide, B.P. 96°–97° C./0.05 mm.Hg., purified by distillation and prepared from N-benzyl-N-n-butylamine.

IX. N-benzyl-2,2-dimethoxy-N-phenyl-acetamide, B.P. 110°–112° C./0.03 mm.Hg., purified by distillation and prepared from N-benzyl-N-phenylamine.

X. 2,2-dimethoxy-N-(3,4-dimethoxybenzyl)-N-(3,4-dimethoxyphenethyl)acetamide, colored oil, purified by column chromatography and prepared from N-(3,4-dimethoxybenzyl)-N-(3,4-dimethoxyphenethyl)amine.

In order to illustrate the usefulness of the new compounds according to the present invention, the acetamides obtained in the Examples given below were cyclized by heating in acid medium at about 70°–95° C. in 70–80% sulfuric acid or in polyphosphoric acid, to give the 2H-3-isoquinolones set out in the following Table:

TABLE

| acetamide of Example No. | 2H-3-isoquinolone formed | M.P. (° C.) | hydrate | yield (%) |
|---|---|---|---|---|
| 1 | 2H-3-isoquinolone | 194–195 (dec.) | — | 63 |
| 2 | 1-methyl-2H-3-isoquinolone | 208–209 (dec.) | + 1H$_2$O | 63 |
| 3 | 1-butyl-2H-3-isoquinolone | 122–124 | — | 28 |
| 4 | 8-chloro-2H-3-isoquinolone | 215–217 (dec.) | + 1H$_2$O | 51 |
| 6 | 6,7-dimethoxy-2H-3-isoquinolone | 238–240 (dec.) | + 3H$_2$O | 91 |
| 7 | 6-methyl-2H-3-isoquinolone | 259–260 (dec.) | + 1H$_2$O | 90 |
| 8 | 1-phenyl-2H-3-isoquinolone | 204–204 | + 1H$_2$O | 32 |
| 11 | N-methyl-2H-3-isoquinolone | 214(phosphate) 194(picrate) (dec.) | | 85 |
| 12 | N-benzyl-2H-3-isoquinolone | 129(HCl) 113(phosphate) | | 93 |

We claim:
1. An N-benzyl-2,2-dimethoxy-acetamide of the formula

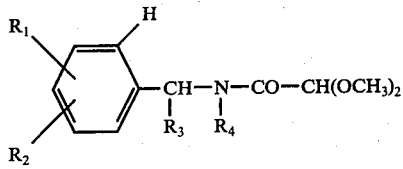

wherein
$R_a$ and $R_2$ each represents hydrogen, halogen, alkyl having 1 to 6 carbon atoms, alkoxy having 1 to 6 carbon atoms, phenyl or naphthyl, said phenyl and naphthyl being unsubstituted or substituted by halogen, alkyl having 1 to 6 carbon atoms or alkoxy having 1 to 6 carbon atoms,
$R_3$ is hydrogen, alkyl having 1 to 6 carbon atoms, phenyl, naphthyl, benzyl, phenethyl, cyclopentyl or cyclohexyl, said phenyl, naphthyl, benzyl, phenethyl, cyclopentyl and cyclohexyl being unsubstituted or ring-substituted by halogen, alkyl having 1 to 6 carbon atoms or alkoxy having 1 to 6 carbon atoms, and
$R_4$ is hydrogen, alkyl having 1 to 6 carbon atoms, phenyl, naphthyl, benzyl or phenethyl, said phenyl, naphthyl, benzyl and phenethyl being unsubstituted or ring-substituted by halogen, alkyl having 1 to 6 carbon atoms or alkoxy having 1 to 6 carbon atoms.

2. A compound as claimed in claim 1, namely N-benzyl-2,2-dimethoxy-acetamide.
3. A compound as claimed in claim 1, namely 2,2-dimethoxy-N-(alpha-methylbenzyl)-acetamide.
4. A compound as claimed in claim 1, namely N-(alpha-n-butyl-benzyl)-2,2-dimethoxy-acetamide.
5. A compound as claimed in claim 1, namely N-(2-chlorobenzyl)-2,2-dimethoxy-acetamide.
6. A compound as claimed in claim 1, namely 2,2-dimethoxy-N-(3-methoxybenzyl)-acetamide.
7. A compound as claimed in claim 1, namely 2,2-dimethoxy-N-(3,4-dimethoxybenzyl)-acetamide.
8. A compound as claimed in claim 1, namely 2,2-dimethoxy-N-(4-methylbenzyl)-acetamide.
9. A compound as claimed in claim 1, namely N-benzhydryl-2,2-dimethoxy-acetamide.
10. A compound as claimed in claim 1, namely 2,2-dimethoxy-N-(alpha-phenylmethyl-benzyl)-acetamide.
11. A compound as claimed in claim 1, namely N-benzyl-2,2-dimethoxy-N-methyl-acetamide.
12. A compound as claimed in claim 1, namely N,N-dibenzyl-2,2-dimethoxy-acetamide.
13. A compound as claimed in claim 1, namely N-benzyl-N-n-butyl-2,2-dimethoxy-acetamide.
14. A compound as claimed in claim 1, namely N-benzyl-2,2-dimethoxy-N-phenyl-acetamide.
15. A compound as claimed in claim 1, namely 2,2-dimethoxy-N-(3,4-dimethoxybenzyl)-N-(3,4-dimethoxyphenethyl)-acetamide.
16. A compound as claimed in claim 1, wherein $R_1$ is hydrogen, halogen, alkyl having 1 to 4 carbon atoms or alkoxy having 1 to 4 carbon atoms, $R_2$ is hydrogen or alkyl having 1 to 4 carbon atoms, $R_3$ is hydrogen, alkyl having 1 to 4 carbon atoms, phenyl, naphthyl, benzyl or phenethyl, and $R_4$ is hydrogen, alkyl having 1 to 4 carbon atoms, phenyl, naphthyl, benzyl or phenethyl.
17. A process for the preparation of an N-benzyl-2,2-dimethoxy-acetamide as claimed in claim 1, which comprises reacting 2,2-dimethoxy-acetyl chloride with a benzylamine of the formula $R_1(R_2)C_6H_3$—$_{CHR3}$—NHR$_4$, wherein $R_1$, $R_2$, $R_3$ and $R_4$ have the meanings given in claim 20, at a temperature of from −60° C to ambient temperature, in an inert organic solvent, in the presence of an acid acceptor.
18. A process for the preparation of an N-benzyl-2,2-dimethoxy-acetamide as claimed in claim 1, which comprises reacting 2,2-dimethoxyacetic acid with 3-chloro-N,N,2-trimethylallylamine in an inert organic solvent and reacting the resulting 2,2-dimethoxy-acetyl chloride, without isolation from the reaction mixture, with a benzylamine of the formula $R_1(R_2)C_6H_3$—CHR$_3$—NHR$_4$, wherein $R_1$, $R_2$, $R_3$ and $R_4$ have the meanings given in claim 1, at a temperature of from −60° C to ambient temperature, in the presence of an acid acceptor.
19. A process as claimed in claim 18, wherein the reaction of 2,2-dimethoxyacetic acid with 3-chloro-N,N,2-trimethyl-allylamine is carried out at a temperature of about −70° C.
20. A process for the preparation of an N-benzyl-2,2-dimethoxyacetamide as claimed in claim 1, $R_4$ being hydrogen, which comprises reacting methyl 2,2-dimethoxyacetate with a benzylamine of the formula $R_1(R_2)C_6H_3$—CHR$_3$—NH$_2$, wherein $R_1$, $R_2$ and $R_3$ have the meanings given in claim 1.
21. A process as claimed in claim 20, wherein the reaction is carried out in the presence of sodium methylate.

* * * * *